United States Patent [19]

Hill et al.

[11] 4,233,295

[45] Nov. 11, 1980

[54] CORTICOSTEROID FORMULATIONS CONTAINING SEBACATE CARRIER

[75] Inventors: John A. Hill, New Brunswick; Yu-chang J. Wang; Thomas M. Wong, both of North Brunswick, all of N.J.

[73] Assignee: E. R. Squibb & Sons, Inc., Princeton, N.J.

[21] Appl. No.: 43,989

[22] Filed: May 31, 1979

[51] Int. Cl.$^3$ .................... A01N 45/00; A61K 31/56
[52] U.S. Cl. .................................................. 424/238
[58] Field of Search ........................................ 424/238

[56] References Cited

U.S. PATENT DOCUMENTS

| | | | |
|---|---|---|---|
| 3,826,845 | 7/1974 | Suyama et al. | 424/238 |
| 4,048,309 | 9/1977 | Chen et al. | 424/238 |
| 4,048,310 | 9/1977 | Chen et al. | 424/238 |
| 4,082,881 | 4/1978 | Chen et al. | 424/238 |

*Primary Examiner*—Elbert L. Roberts
*Attorney, Agent, or Firm*—Lawrence S. Levinson; Burton Rodney

[57] ABSTRACT

Corticosteroid formulations in the form of creams, lotions or ointments are provided which are used as anti-inflammatory agents, wherein the corticosteroid, such as halcinonide (21-chloro-9-fluoro-11$\beta$-hydroxy-16$\alpha$,17-[(1-methylethylidene)-bis(oxy)]pregn-4-ene-3,20-dione) is dissolved in a sebacate carrier, such as dibutyl sebacate.

16 Claims, No Drawings

CORTICOSTEROID FORMULATIONS CONTAINING SEBACATE CARRIER

DESCRIPTION OF THE INVENTION

The present invention relates to pharmaceutical formulations which include a dialkyl sebacate, such as dibutyl sebacate or diisopropyl sebacate as a vehicle for the pharmaceutical.

Topical corticosteroid formulations are extensively employed in the treatment of skin disorders, such as dermatitis. To be therapeutically effective, the active ingredient preferably should be in a molecular dispersion to facilitate desired percutaneous absorption which is particularly important in achieving a therapeutic response for the management of psoriasis. Unfortunately, many of the desirable steroids are insoluble in water and even less soluble in hydrocarbon vehicles such as mineral oil, petrolatum or polyethylene gelled mineral oil.

Various organic solvents and solubilizers have been found to be good solvents for steroids. However, many of such solvents have been found to be unsuitable for commercial application for reasons such as their high volatility and low boiling points, their disagreeable odor, their "paint removing" property, or their undesirable skin reaction. Furthermore, various water-soluble or water-dispersible emulsifiers and oil liquids or emollients have been suggested for use in preparing ointments, gels, creams and lotions. However, because of the undesirably low solubility of the steroid in many such vehicles, higher levels of these materials in topical products are required thereby increasing their cost and also adversely affecting their cosmetic elegance.

Accordingly, in view of the above considerations, it is seen that a need exists for a suitable vehicle capable of solubilizing a sufficient amount of the steroid so that it may be employed in a topical formulation, while being dermatologically beneficial, stable, and pharmaceutically acceptable.

In accordance with the present invention, it has now been found that sebacates, such as dialkyl sebacates, wherein alkyl contains 1 to 10 carbons, for example, dibutyl sebacate and diisopropyl sebacate, are excellent vehicles for corticosteroids.

The active ingredient employed in the formulations of the invention will preferably comprise a steroid which will be present in an amount of from about 0.001 to about 3% by weight, and preferably from about 0.025 to about 0.2% based on the total weight of the composition, depending upon the type of steroid employed and its solubility in the sebacate containing vehicle.

Exemplary of the steroids contemplated are the acetonide derivatives of steroids of the pregnane series described in U.S. Pat. Nos. 3,048,581 and 3,937,720. Included within the steroids described by the former patent is halcinonide In addition, the sebacate may be employed to dissolve steroids disclosed in U.S. Pat. Nos. 3,976,637, 3,979,417, 3,994,935, 4,018,757, 4,116,978, 4,018,774, 4,091,036, 4,094,840, 4,133,811 and 4,146,538, U.S. application Ser. No. 919,006, filed June 26, 1978, now U.S. Pat. No. 4,160,772 and U.S. application Ser. No. 919,020, filed June 26, 1978, now U.S. Pat. No. 4,164,504.

In preferred embodiments, dibutyl sebacate or diisopropyl sebacate are employed to dissolve halcinonide, 21-(acetyloxy)-9-fluoro-1',2',3',4'-tetrahydro-11$\beta$-hydroxypregna-1,4dieno[16$\alpha$,17-b]-naphthalene-3,20-dione, 21-chloro-9-fluoro-1',2'-3',4'-tetrahydro-11$\beta$-hydroxypregna-1,4-dieno[16$\alpha$,-17-b]naphthalene-3,20-dione, (11$\beta$,16$\alpha$)-9-fluoro-1',2',3',4'-tetrahydro-11-hydroxy-3,20-dioxopregna-1,4-dieno[16$\alpha$,17-b]naphthalen-21-oic acid, 1-methylethyl ester, or (11$\beta$,16$\alpha$)-9-fluoro-11-hydroxy-3,20-dioxopregna-1,4-dieno[16,17-d]cyclohexen-21-oic acid, 1-methylethyl ester. It is emphasized that these steroids are meant to be exemplary only and it is not meant to limit this invention to use with any particular steroid or group of topically active anti-inflammatory steroids.

The sebacate will be present in the compositions of the invention in amounts within the range of from about 5 to about 95% and more depending upon the type of pharmaceutical composition and the active ingredient contained therein.

The formulations employing the sebacate vehicle in accordance with the present invention may take the form of a hydrophobic base such as an ointment (non-aqueous) or gel, as well as a cream, lotion, and liquid including parenterals, nose drops, ear drops and the like.

The lotion or cream includes the sebacate as the oil phase. The lotions and creams of the invention will include the active ingredient "all-in-solution" so that substantially no active ingredient crystallizes out at room temperature.

With regard to the cream formulations of the invention where the steroid is to be all-in-solution, the cream will contain from about 0.005 to about 0.6% and preferably from about 0.025 to about 0.2% by weight of the active ingredient based on the weight of the entire cream formulation, and from about 5 to about 75% and preferably from about 10 to about 50% by weight of the sebacate based on the weight of the entire cream formulation and depending upon the solubility of the particular active ingredient in the particular sebacate employed. The all-in-solution cream formulation will include substantially all of the active ingredient in the oily sebacate phase.

Where present, an anti-whitening agent or anti-foaming agent will comprise a separate oil phase and will be present in an amount within the range of from about 0.2 to about 3% and preferably from about 0.5 to about 1.5% by weight based on the entire cream formulation. An antioxidant may also optionally be included in an amount within the range of from about 0.005 to about 0.1% and preferably from about 0.01 to about 0.05% by weight based on the entire cream formulation.

The aqueous phase of the all-in-solution cream formulation may contain a glycol type preservative such as propylene glycol in an amount within the range of from about 2 to about 50% and preferably from about 4 to 40% by weight of the entire cream formulation and/or a paraben or other conventional type preservative such as methyl and/or propyl paraben in an amount ranging from about 0.05 to about 0.5%, and purified water in an amount within the range of from about 30 to about 70% by weight and preferably from about 35 to about 65% by weight of the entire cream formulation.

With regard to the lotion formulation of the invention where the steroid is to be all-in-solution, the lotion will contain from about 0.005 to about 0.6% and preferably from about 0.02 to about 0.05% by weight of the active ingredient based on the weight of the entire lotion formulation, and from about 5 to about 75% and preferably from about 10 to about 50% by weight of the sebacate based on the weight of the entire lotion formulation, depending upon the solubility of the particular ingredient in the sebacate.

The above lotions or creams may contain from abut 5 to about 14% and preferably from about 8 to about 12% by weight emulsifier-thickener (such as, cetyl alcohol) based on the weight of the entire lotion formulation.

In general, emulsifier-thickeners suitable for use herein may comprise ethers of polyethylene glycol and fatty alcohols, such as, Promulgen, Robinson Wagner Co., which contains some unreacted cetyl and stearyl alcohol, and other non-ionic emulsifying waxes such as Polawax, Croda Co.

The same emulsifier-thickener used in the formulations of the invention may also be obtained by substituting the above-mentioned emulsifying waxes with a mixture of polyoxyethylene (20) stearyl alcohol ether (BRIJ 78, ICI) or polyoxyethylene (20) cetyl alcohol ether (BRIJ 58, ICI) with cetyl or stearyl alcohol. The ratio of the BRIJ or a mixture of the two BRIJ with the fatty alcohol or a mixture of the two alcohols should be within the range of from about 0.6 to about 3.5, preferably from about 1 to about 3.

Another emulsifier system suitable for use in the invention comprises a combination of glyceryl monostearate with polyoxyethylene sorbitan palmitate or stearate and stearyl alcohol. For example, a cream or lotion containing 0.025% by weight halcinonide in dibutyl sebacate (5-50%), an oil-in-water cream, can be made with glyceryl monostearate (1-8%), cetyl alcohol (2-6%) and Tween 60 (polyoxyethylene sorbitan monostearate 2-7.1%).

It will also be appreciated that two or more materials may be employed to provide the emulsifying function and the thickening function. Thus, examples of emulsifying agents suitable for use herein include propylene glycol monostearate, as well as the non-ionic polyoxyalkylene derivatives of hexitol anhydride partial long chain fatty acid esters, e.g., the polyoxyalkylene derivative of sorbitan monolaurate, sorbitan monopalmitate, sorbitan monostearate, sorbitan tristearate, sorbitan monooleate or sorbitan trioleate. These emulsifying agents are commercially available as Tween 20, 21, 40, 60, 65, 80, 81 and 85.

Thickeners suitable for use in combination with the above emulsifying agents include those conveniently employed in topical creams, such as, for example, monoglycerides and fatty alcohols, fatty acid esters of alcohols having from about 3 to about 16 carbon atoms. Examples of suitable monoglycerides are glyceryl monostearate and glyceryl monopalmitate. Examples of fatty alcohols are cetyl alcohol and stearyl alcohol. Examples of suitable esters are myristyl stearate and cetyl stearate. The monoglyceride also functions as an auxiliary emulsifier. Other emollients or oleaginous materials which may be employed include petrolatum, glyceryl monooleate, myristyl alcohol and isopropyl palmitate.

A second oil phase may also optionally include an anti-whitening agent or anti-foaming agent, such as silicone fluid, in an amount within the range of from about 0.2 to about 3% and preferably from about 0.5 to about 1.5% by weight based on the entire lotion formulation. An anti-oxidant may also optionally be included in an amount within the range of from about 0.005 to about 0.1% and preferably from about 0.01 to about 0.05% by weight based on the entire lotion formulation.

The aqueous phase of the all-in-solution lotion formulation may contain a glycol-type preservative, such as propylene glycol or 1,3-butylene glycol, in an amount within the range of from about 5 to about 50% and preferably from about 12 to about 40% by weight of the entire lotion formulation, and/or parabens (p-hydroxy benzoates) or other conventional type preservative in an amount ranging from about 0.05 to about 0.5%, and purified water in an amount within the range of from about 50 to about 90% by weight and preferably from about 60 to about 85% by weight of the entire lotion formulation.

Where the active ingredient is to be employed in parenteral solutions, the sebacate vehicle will be present in amounts ranging from about 80 to about 99%, and preferably from about 85 to about 98%; the concentration of the active ingredient will vary depending upon the type employed and will range from about 0.01 to about 2.5% by weight. A 1 to 5% ethanol solution may be used to enhance clarity of the product.

When the formulation of the invention is in the form of nose drops or ear drops, the sebacate vehicle will be present in amounts ranging from about 80 to about 99% and preferably from about 85 to about 98% by weight while the active ingredient will vary depending upon the type used.

With regard to specific steroid formulations, where halcinonide is employed in all-in-solution creams or lotions, the sebacate vehicle will be preferably employed in an amount within the range of from about 30 to about 70% by weight and more preferably within the range of from about 40 to about 60% by weight, while the steroid will be present in amounts ranging from about 0.02 to about 0.2% by weight.

Where 21-(acetyloxy)-9-fluoro-1',2',3',4'-tetrahydro-11$\beta$-hydroxypregna-1,4-dieno[16$\alpha$,17-b]-naphthalene-3,20-dione is employed in all-in-solution creams or lotions, the sebacate vehicle will be preferably employed in an amount within the range of from about 5 to about 50% by weight and more preferably within the range of from about 5 to about 30% by weight while the steroid will be employed in amounts ranging from about 0.02 to about 0.2% by weight.

Where other steroids are employed in a cream or lotion, the sebacate vehicle will be preferably employed in amounts within the range of from about 5 to about 75% by weight and preferably from about 10 to about 50% by weight while the active steroid may be employed in amounts within the range of from about 0.001 to about 0.2% by weight.

The hydrophobic formulations of the invention which include non-aqueous ointments, gels and the like, comprise a steroid as described herein, a sebacate vehicle and oleaginous material, and optionally a wax and/or antioxidant.

The oleaginous material will generally be present in an amount within the range of from about 25 to about 99% by weight, and preferably from about 50 to about 90% by weight.

The ointiments of the invention may include the active steroid ingredient solubilized in the continuous sebacate phase.

The ointment will contain from about 0.001 to about 2%, and preferably from about 0.025 to about 0.2% by weight of the steroid ingredient, and from about 5 to about 75% and preferably from about 5 to about 65% by weight of the sebacate based on the weight of the entire ointment formulation and depending upon the solubility of the particular active ingredient in the particular sebacate employed. The all-in-solution ointment formulation (exclusive of the gel) will also include, in addition to the active ingredient and sebacate, from about 25 to about 95% and preferably from about 85 to about 95% by weight of oleaginous material based on the weight of the entire formulation. The formulation may also optionally include an opacifying agent, such as titanium dioxide, serving as indicator for homogeneity of dispersion, in an amount within the range of from about 0.2 to about 1% and preferably from about 0.3 to about 0.8% by weight based on the entire formulation. An antioxidant may also optionally be included in an amount within the range of from about 0.005 to about 0.1% and preferably from about 0.01 to about 0.05% by weight based on the entire formulation.

Examples of oleaginous material suitable for use herein are petrolatum, other sebacate miscible or immiscible oily material and mineral oil thickened or gelled with polyethylene, or high molecular weight paraffin waxes or mono and diglycerides of fatty acids gelled with high molecular weight fatty acids and/or polyamide complex of hydroxystearate. Petrolatum (petroleum jelly) is a purified mixture of semisolid hydrocarbons from petroleum having a melting point of from about 45° to about 65° C., preferably from about 50° to about 60° C. When the mixture of active ingredient and sebacate is mechanically dispersed in the oleaginous material, the mixture may be gelled by polyethylene as disclosed in U.S. Pat. Nos. 2,627,938, 2,628,187, 2,628,205 and 3,733,403. The disclosures of the foregoing patents are incorporated herein by reference.

The all-in-solution ointment may simply be prepared by dissolving the active ingredient in the sebacate with gentle heat not over 90° C., cooling to room temperature and then incorporating the same into the oleaginous material by slow mixing until homogeneous. If the steroid is not completely dissolved in the sebacate, then another vehicle such as polyethylene glycol, propylene glycol, butylene glycol, propylene carbonate or other known solvents for steroids may be used to dissolve the undissolved portion of the steroid. Thereafter, the steroid-vehicle combination may be dispersed with the sebacate portion.

The gel formulation of the invention is preferably in the form of a lipophilic gel, and will contain from about 0.005 to about 3%, and preferably from about 0.025 to about 0.5% by weight of the active steroid based on the weight of the entire formulation, and from about 0.5 to about 20% and preferably from about 1 to about 10% by weight of the sebacate based on the weight of the entire formulation, depending upon the solubility of the particular active steroid. The formulation may also optionally include a surfactant, such as Span 65 (sorbitan tristearate), as well as Span 60 (sorbitan monostearate), Span 40 (sorbitan monopalmitate), butylene glycol distearate in amounts up to about 8% by weight based on the entire formulation. An antioxidant, such as butylated hydroxyanisole or butylated hydroxytoluene may also optionally be included in amounts up to about 0.1% and preferably up to about 0.05% by weight based on the entire formulation.

In the non-aqueous gel formulation of the invention, various gelling agents may be employed to gel the sebacate, such as waxes, for example, high molecular weight paraffin wax (Paraflint RG), propylene glycol isostearate (Emery 2389A), polyamide complex of hydroxystearate (Acrowax, Glyco), carnauba wax, white wax, ozokerite and/or candelilla wax.

With regard to specific steroid ointment or gel formulations, where halcinonide is employed in all-in-solution ointments, the sebacate vehicle will be preferably employed in an amount within the range of from about 10 to about 90% by weight and more preferably within the range of from about 25 to about 65% by weight, while the steroid will be employed in amounts ranging from about 0.001 to about 1% by weight.

Where 21-(acetyloxy)-9-fluoro-1',2',3',4'-tetrahydro-11β-hydroxypregna-1,4-dieno[16α,17-b]-naphthalene-3,20-dione is employed in all-in-solution ointments the sebacate vehicle will be preferably employed in an amount within the range of from about 10 to about 90% by weight and more preferably within the range of from about 25 to about 65% by weight while the steroid will be employed in amounts ranging from about 0.001 to about 1% by weight.

In the case of ointments and lipophilic gels where the formulation is substantially free of water, the active ingredient will be dissolved in the sebacate vehicle and, in part, in other vehicles which may be employed as described hereinbefore.

The cream, lotion or ointment may also contain an antioxidant such as butylated hydroxytoluene, butylated hydroxyanisole and the like for protecting the active ingredient against oxidation.

Examples of preferred dibutyl sebacate or diisopropyl sebacate vehicles in accordance with the present invention include, but are not limited to, the following.

| Aqueous Cream for Moderately Insoluble Steroids | |
|---|---|
| | Parts by Weight |
| Dibutyl of Diisopropyl sebacate | 15 to 25 |
| Polysorbate 60 | 2 to 8 |
| Glyceryl stearate | 3 to 10 |
| White wax | 1 to 5 |
| Preservative (propylene glycol) | 6 to 15 |
| Anti-foam agent (dimethicone) | 0 to 2 |
| Water  q.s to make | 100 parts |

| Aqueous Cream for Insoluble Steroids | |
|---|---|
| | Parts by Weight |
| Dibutyl or Diisopropyl sebacate | 25 to 60 |
| Glyceryl stearate | 1 to 5 |
| White wax | 3 to 7 |
| Promulgen D (cetearyl alcohol and ceteareth-20), Robinson-Wagner | 4 to 10 |
| Dimethicone | 0 to 2 |
| Propylene glycol | 5 to 20 |
| Water  q.s. to make | 100 parts |

| Anhydrous Gels | | | |
|---|---|---|---|
| | Parts by Weight | | |
| | 1 | 2 | 3 |
| Dibutyl or diisopropyl sebacate | 85 to 95 | 80 to 92 | 65 to 75 |
| Carnauba wax | 15 to 50 | | |
| Polyethylene | | 20 to 8 | 10 to 15 |
| Mineral oil | | | 15 to 20 |

Examples of preferred steroid formulations in accordance with the present invention include, but are not limited to, the following:

| Halcinonide Topical Cream, 0.025% | |
|---|---|
| | Ranges |
| Halcinonide, micronized | 0.022–0.03 gm. |
| Dibutyl or diisopropyl sebacate | 6–10 gm. |
| Polysorbate 60 | 2–8 gm. |

| | |
|---|---|
| or | or |
| Promulgen, Type D (Cetearyl alcohol & Ceteareth-20), Robinson-Wagner | 4–10 gm. |
| Glyceryl stearate | 1–5 gm. |
| White wax | 3–7 gm. |
| Propylene glycol | 5–15 gm. |
| Dimethicone 350 | 0–2 gm. |
| Purified water,  q.s. | 100.0 gm. |

| Halcinonide Topical Cream, 0.1% | |
|---|---|
| | Ranges |
| Halcinonide, micronized | 0.09–0.11 gm. |
| Dibutyl or Diisopropyl sebacate | 25–35 gm. |
| Polysorbate 60 | 2–8 gm. |
| or | or |
| Promulgen, Type D (Cetearyl alcohol & Ceteareth-20), Robinson-Wagner | 4–10 gm. |
| Glyceryl monostearate | 1–5 gm. |
| White wax | 3–7 gm. |
| Propylene glycol | 5–15 gm. |
| Dimethicone 350 | 0–2 gm. |
| Purified water,  q.s. | 100.0 gm. |

| Topical Cream Containing 0.025% 21-(Acetyloxy)-9-fluoro-1',2',3',4'-tetrahydro-11β-hydroxypregna-1,4-dieno[16α,17-b]naphthalene-3,20-dione | |
|---|---|
| Steroid, micronized | 0.02–0.03 gm. |
| Dibutyl or Diisopropyl sebacate | 3–10 gm. |
| Polysorbate 60 | 2–8 gm. |
| or | or |
| Promulgen D | 4–10 gm. |
| Glyceryl monostearate | 1–5 gm. |
| White wax | 3–7 gm. |
| Propylene glycol | 5–15 gm. |
| Dimethicone 350 | 0–2 gm. |
| Purified water 0.50 | 100.0 gm. |

| Topical Cream Containing 0.1% 21-(Acetyloxy)-9-fluoro-1', 2', 3', 4'-tetrahydro-11β-hydroxypregna-1,4-dieno[16α-,17-b]naphthalene-3,20-dione | |
|---|---|
| | Ranges |
| Steroid, micronized | 0.09–0.11 gm. |
| Dibutyl or Diisopropyl sebacate | 15–25 gm. |
| Polysorbate 60 | 2–8 gm. |
| or | or |
| Promulgen, Type D (Cetearyl alcohol & Ceteareth-20), Robinson-Wagner | 4–10 gm. |
| Glyceryl monostearate | 1–5 gm. |
| White wax | 3–7 gm. |
| Propylene glycol | 5–15 gm. |
| Dimethicone 350 | 0–2 gm. |
| Purified water,  q.s. | 100.0 gm. |

| Halcinonide Lotion 0.025% | |
|---|---|
| Halcinonide, micronized | 0.02–0.03 gm. |
| Dibutyl or Diisopropyl sebacate | 3–10 gm. |
| Polysorbate 60 | 2–8 gm. |
| Sodium carboxymethyl cellulose | 2–8 gm. |
| Cetyl alcohol | 1–3 gm. |
| Propylene glycol | 5–15 gm. |
| Purified water,  q.s. | 100.0 gm. |

| Lotion Containing 0.025% 21-(Acetyloxy)-9-fluoro-1',2',3',4'-tetrahydro-11β-hydroxypregna-1,4-dieno[16α,17-b]naphthalene-3,20-dione | |
|---|---|
| | Ranges |
| Steroid, micronized | 0.02–0.03 gm. |
| Dibutyl or Diisopropyl sebacate | 3–10 gm. |
| Polysorbate 60 | 2–8 gm. |
| Sodium carboxymethyl cellulose | 2–8 gm. |
| Cetyl alcohol | 1–3 gm. |
| Methyl paraben | 0.1–0.5 gm. |
| Propyl paraben | 0.01–0.05 gm. |
| Purified water,  q.s. | 100.0 gm. |

| Intramuscular Injection Containing 4% 21-(Acetyloxy)-9-fluoro-1',2',3',4'-tetrahydro-11β-hydroxypregna-1,4-dieno[16α,17-b]naphthalene-3,20-dione | |
|---|---|
| Steroid | 4 gm. |
| Benzyl alcohol | 0.5–2.5 gm. |
| Dibutyl sebacate sufficient to make | 100 ml. |

The following examples illustrate preferred embodiments of the present invention without, however, limiting the same thereto. All temperatures are expressed in degrees Centigrade.

EXAMPLE 1

| Cream Containing 0.025% 21-(Acetyloxy)-9-fluoro-1',2',3',4'-tetrahydro-11β-hydroxypregna-1,4-dieno-[16α,17-b]naphthalene-3,20-dione (all-in-solution) | |
|---|---|
| Steroid, micronized | 0.025 gm. |
| Dibutyl sebacate | 5 gm. |
| Glyceryl stearate | 4 gm. |
| White wax | 4 gm. |
| Promulgen, Type D (PEG fatty alcohol ether)-Cetearyl alcohol & Ceteareth-20 (Robinson-Wagner) | 7 gm. |
| Propylene glycol | 15 gm. |
| Dimethicone 350 | 1 gm. |
| Purified water, sufficient to make | 100.0 gm. |

The steroid is dissolved in dibutyl sebacate with gentle heat not over 90° C. The glyceryl stearate, white wax, Dimethicone 350 and Promulgen are melted together and heated to 75°–80° C. and then mixed with the above steroid solution and the propylene glycol. The resulting mixture is added to hot 75°–80° C. purified water with vigorous agitation to emulsify. Agitation is continued until the temperature drops down to 48° C. Sufficient hot (48°–50° C.) purified water is then added to make 100 gm. Mixing is then continued at a slow rate during the congealing stage until the cream reaches room temperature.

EXAMPLE 2

| Halcinonide Cream 0.025% | |
|---|---|
| Halcinonide, micronized | 0.025 gm. |
| Dibutyl sebacate | 7 gm. |
| Glyceryl stearate | 4 gm. |
| White wax | 4 gm. |
| Promulgen, Type D (PEG fatty alcohol ether)-Cetearyl alcohol & Ceteareth-20 (Robinson-Wagner) | 7 gm. |
| Propylene glycol | 15 gm. |
| Dimethicone 350 | 1 gm. |
| Purified water, sufficient to make | 100.0 gm. |

The above cream is prepared employing the procedure of Example 1.

EXAMPLE 3

| Halcinonide Cream 0.1% | |
|---|---|
| Halcinonide, micronized | 0.1 gm. |
| Dibutyl sebacate | 30 gm. |
| Glyceryl stearate | 4 gm. |
| White wax | 4 gm. |
| Promulgen, Type D (PEG fatty alcohol ether)-Cetearyl alcohol & Ceteareth-20 (Robinson-Wagner) | 9 gm. |
| Propylene glycol | 11 gm. |

-continued

| Halcinonide Cream 0.1% | |
| --- | --- |
| Dimethicone 350 | 1 gm. |
| Purified water, sufficient to make | 100.0 gm. |

The above cream is prepared employing the procedure described in Example 1.

EXAMPLE 4

| Cream Containing 0.1% 21-(Acetyloxy-9-fluoro-1',2',-3',4'-tetrahydro-11β-hydroxypregna-1,4-dieno[16β,17-b]-naphthalene-3,20-dione | |
| --- | --- |
| Steroid | 0.1 gm. |
| Dibutyl sebacate | 18 gm. |
| Glyceryl stearate | 4 gm. |
| White wax | 4 gm. |
| Promulgen, Type D (PEG fatty alcohol ether)-Cetearyl alcohol & Ceteareth-20 (Robinson-Wagner) | 9 gm. |
| Propylene glycol | 11 gm. |
| Dimethicone 350 | 1 gm. |
| Purified water, sufficient to make | 100.0 gm. |

The above cream is prepared as described in Example 1.

EXAMPLE 5

| Halcinonide Lotion 0.025% | |
| --- | --- |
| Halcinonide, micronized | 0.025 gm. |
| Dibutyl sebacate | 7 gm. |
| Polysorbate 60 | 5 gm. |
| Sodium carboxymethyl cellulose | 5 gm. |
| Cetyl alcohol | 2 gm. |
| Methylparaben | 0.3 gm. |
| Propylparaben | 0.03 gm. |
| Purified water, q.s. | 100 gm. |

The steroid and parabens are dissolved in dibutyl sebacate with gentle heat, not over 90° C. and melted together and Polysorbate 60 and cetyl alcohol added, while maintaining the temperature at 75°–80° C. Water is heated to 80° C. to dissolve the sodium carboxymethyl cellulose forming an aqueous phase which is added with vigorous agitation to the oil phase to emulsify. Agitation is continued until the temperature drops down to 48° C. Sufficient 50° C. water is added to make 100 gm. Mixing is continued at a slow rate to congeal the mixture, until the lotion drops down to room temperature.

EXAMPLE 6

| Lotion Containing 0.025% 21-(Acetyloxy)-9-fluoro-1',2',3',4'-tetrahydro-11β-hydroxypregna-1,4-dieno[16α-17-b]naphthalene-3,20-dione | |
| --- | --- |
| Steroid, micronized | 0.025 gm. |
| Dibutyl sebacate | 5 gm. |
| Polysorbate 60 | 5 gm. |
| Sodium carboxymethyl cellulose | 5 gm. |
| Cetyl alcohol | 2 gm. |
| Methylparaben | 0.3 gm. |
| Propylparaben | 0.03 gm. |
| Purified water, q.s. | 100 gm. |

The above lotion is prepared employing the procedure of Example 5.

EXAMPLE 7

| Intramuscular Injection Containing 4% 21-(Acetyloxy)-9-fluoro-1',2',3',4'-tetrahydro-11β-hydroxypregna-1,4-dieno[16α,17-b]naphthalene-3,20-dione | |
| --- | --- |
| Steroid | 4 gm. |
| Benzyl alcohol | 2 gm. |
| Dibutyl sebacate sufficient to make | 100 gm. |

The above injectable is prepared by simply mixing and sterilizing the above ingredients.

EXAMPLE 8

| Cream Containing 0.1% 21-Chloro-9-fluoro-1',2',3',4'-tetrahydro-11β-hydroxypregna-1,4-dieno[16α,17-b]-naphthalene-3,20-dione | |
| --- | --- |
| Steroid | 0.1 gm. |
| Diisopropyl sebacate | 35 gm. |
| Glyceryl stearate | 5 gm. |
| White wax | 4 gm. |
| Promulgen | 7 gm. |
| Dimethicone | 1 gm. |
| Propylene glycol | 12 gm. |
| Purified water, q.s. to make | 100 gm. |

The above cream is prepared employing procedures similar to that described in Example 1.

EXAMPLE 9

| Cream Containing 0.2% (11β,16α)-9-Fluoro,1',2',3',4'-tetrahydro-11-hydroxy-3,20-dioxopregna-1,4-dieno-[16α,17-b]naphthalen-21-oic acid, 1-methylethyl ester | |
| --- | --- |
| Steroid | 0.2 gm. |
| Dibutyl sebacate | 15 gm. |
| Glyceryl stearate | 5 gm. |
| White wax | 4 gm. |
| Polysorbate 60 | 5 gm. |
| Dimethicone | 1 gm. |
| Propylene glycol | 15 gm. |
| Purified water q.s. to | 100 gm. |

The above cream is prepared employing procedures as described in Example 1.

EXAMPLE 10

| Ointment, 0.025% (all-in-solution) | |
| --- | --- |
| Halcinonide, micronized | 0.025 gm. |
| (a) Dibutyl sebacate | 50 gm. |
| (b) Mineral Oil | 44 gm. |
| (a) and (b) gelled with polyethylene) | 5 gm. |
| Titanium dioxide | 0.5 gm. |

The steroid is dissolved in dibutyl sebacate, and mineral oil and polyethylene are added to the solution with gentle heat not over 90° C. The mixture is heated to 120° C. until homogeneous. The mixture is shock cooled to room temperature and titanium dioxide is dispersed homogeneously therein.

EXAMPLE 11

| Lipophilic gel, 0.025% (all-in-solution) | |
| --- | --- |
| Halcinonide, micronized | 0.025 gm. |
| Dibutyl sebacate | 92 gm. |

-continued

| Lipophilic gel, 0.025% (all-in-solution) | |
|---|---|
| Carnauba wax | 8 gm. |

The steroid is dissolved in dibutyl sebacate by gentle heat (70° C.). The carnauba wax is added, allowed to dissolve, and the melted mass shockcooled by pouring the solution onto a cold surface.

The gel obtained is a smooth, glossy semisolid ointment-like gel.

What is claimed is:

1. A steroid composition in the form of an ointment, gel, lotion, cream or solution which is useful in treating dermatitis, consisting essentially of an effective amount of from about 0.001 to about 3% by weight of a corticosteroid and a dialkyl sebacate in an amount of from about 5 to about 75% by weight of the composition, the corticosteroid being dissolved in the dialkyl sebacate.

2. The steroid composition as defined in claim 1 wherein said sebacate vehicle is present in an amount within the range of from about 5 to about 95% by weight of the composition.

3. The steroid composition as defined in claim 1 in the form of an ointment, gel, lotion, cream or solution.

4. The steroid composition as defined in claim 1 wherein said sebacate is dibutyl sebacate.

5. The steroid composition as defined in claim 1 wherein said sebacate is diisopropyl sebacate.

6. The steroid composition as defined in claim 1 wherein said steroid is halcinonide or triamcinolone acetonide.

7. The steroid composition as defined in claim 3 in the form of a cream or lotion wherein said steroid is present in an amount within the range of from about 0.005 to about 0.6% by weight of the composition, said sebacate vehicle is present in an amount within the range of from about 5 to about 75% by weight of the composition.

8. The steroid composition as defined in claim 7 and further including an emulsifier-thickener present in an amount within the range of from about 1 to about 14% by weight of the composition, a preservative present in an amount within the range of from about 0.05% to about 50% by weight of the composition, and water present in an amount within the range of from 30 to about 90% by weight of the composition.

9. The composition as defined in claim 3 in the form of a lotion wherein said steroid is all-in-solution, said steroid being present in an amount within the range of from about 0.005 to about 0.6% by weight of the composition, said sebacate being present in an amount within the range of from about 5 to about 75% by weight of the composition.

10. The steroid composition as defined in claim 9 further including an emulsifier-thickener present in an amount within the range of from about 5 to about 14% by weight of the composition, a preservative present in an amount within the range of from about 0.05% to about 50% by weight of the composition, and water present in an amount within the range of from about 50 to about 90% by weight of the composition, and optionally including an anti-oxidant present in an amount within the range of from about 0.005 to about 0.1% by weight of the composition, and further optionally including an anti-whitening agent or anti-foaming agent present in an amount within the range of from about 0.2 to about 3% by weight of the composition.

11. The steroid composition as defined in claim 3 in the form of an ointment or gel wherein said steroid is present in an amount within the range of from about 0.001 to about 2% by weight of the composition, said sebacate vehicle is present in an amount within the range of from about 5 to about 75% by weight of the composition.

12. The steroid composition as defined in claim 11 further including an oleaginous material present in an amount within the range of from about 25 to about 95% by weight of the composition.

13. The steroid composition as defined in claim 12 further including one or more antioxidants.

14. A method of treating dermatitis, which comprises administering topically an effective amount of a composition as defined in claim 1.

15. A method of treating dermatitis, which comprises administering topically an effective amount of a composition as defined in claim 7.

16. A method of treating dermatitis, which comprises administering topically an effective amount of a composition as defined in claim 11.

* * * * *